US009750622B2

(12) United States Patent
Ma et al.

(10) Patent No.: US 9,750,622 B2
(45) Date of Patent: Sep. 5, 2017

(54) HIGH MOLECULAR WEIGHT POLYLACTIDE AND POLYCAPROLACTONE COPOLYMER AND BLENDS FOR BIORESORBABLE VASCULAR SCAFFOLDS

(71) Applicant: Abbott Cardiovascular Systems Inc., Santa Clara, CA (US)

(72) Inventors: Xiao Ma, Santa Clara, CA (US); Mary Beth Kossuth, San Jose, CA (US); James P. Oberhauser, Saratoga, CA (US); Stephen D. Pacetti, San Jose, CA (US); Manish Gada, Santa Clara, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 611 days.

(21) Appl. No.: 14/307,440

(22) Filed: Jun. 17, 2014

(65) Prior Publication Data

US 2015/0359648 A1 Dec. 17, 2015

(51) Int. Cl.
*A61F 2/90* (2013.01)
*A61L 31/14* (2006.01)
(Continued)

(52) U.S. Cl.
CPC ............... *A61F 2/90* (2013.01); *A61F 2/91* (2013.01); *A61L 31/041* (2013.01); *A61L 31/06* (2013.01); *A61L 31/148* (2013.01)

(58) Field of Classification Search
CPC ..... A61F 2/90–2002/91583; A61F 2210/0003; A61F 2230/0069;
(Continued)

(56) References Cited

U.S. PATENT DOCUMENTS

| 8,968,387 B2 * | 3/2015 | Stankus | A61L 31/148 |
| | | | 623/1.19 |
| 2005/0119733 A1 * | 6/2005 | Wiliams | A61F 2/06 |
| | | | 623/1.49 |

(Continued)

FOREIGN PATENT DOCUMENTS

| WO | WO2012158842 A2 * | 11/2012 | ............. A61L 31/14 |
| WO | WO 2013/003644 A1 | 1/2013 | |
| WO | WO 2014/045068 | 3/2014 | |

OTHER PUBLICATIONS

International Search Report and the Written Opinion of the International Searching Authority mailed on Dec. 18, 2015, for related PCT Application No. PCT/US2015/036216, 30 pp.

(Continued)

*Primary Examiner* — Paul Prebilic
(74) *Attorney, Agent, or Firm* — Squire Patton Boggs (US) LLP

(57) ABSTRACT

Bioresorbable polymer vascular scaffolds made of combinations of polylactide and polycaprolactone having a high molecular weight polymer, thin struts in a selected range and sufficient radial strength to support a vessel upon deployment. The scaffolds have degradation behavior of molecular weight, radial strength, and mass that are conducive to healing of a vessel including providing patency to a vessel, reduction of radial strength, breaking up, and resorbing to allow return of the vessel to a natural state.

8 Claims, 4 Drawing Sheets

(51) Int. Cl.
*A61F 2/91* (2013.01)
*A61L 31/06* (2006.01)
*A61L 31/04* (2006.01)

(58) Field of Classification Search
CPC .. A61F 2250/001; A61L 31/04; A61L 31/041; A61L 31/06; A61L 31/148; A61L 31/14; A61L 2430/00; A61L 2430/22
See application file for complete search history.

(56) References Cited

U.S. PATENT DOCUMENTS

| | | |
|---|---|---|
| 2007/0283552 A1 | 12/2007 | Gale et al. |
| 2008/0033540 A1 | 2/2008 | Wang et al. |
| 2008/0147165 A1 | 6/2008 | Hossainy et al. |
| 2008/0275537 A1 | 11/2008 | Limon |
| 2009/0324670 A1 | 12/2009 | Wang |
| 2010/0076556 A1* | 3/2010 | Tomantschger ........ A61L 17/10 623/11.11 |
| 2010/0262224 A1 | 10/2010 | Kleiner |
| 2011/0066222 A1 | 3/2011 | Wang et al. |
| 2011/0130822 A1* | 6/2011 | Cottone .................... A61F 2/91 623/1.15 |
| 2011/0190871 A1 | 8/2011 | Trollsas et al. |
| 2011/0190872 A1 | 8/2011 | Anukhin et al. |
| 2011/0264186 A1* | 10/2011 | Berglung .................. A61F 2/86 623/1.11 |
| 2012/0073733 A1 | 3/2012 | Ngo et al. |
| 2012/0290073 A1 | 11/2012 | Wang et al. |
| 2013/0032967 A1 | 2/2013 | Wang et al. |
| 2013/0138206 A1* | 5/2013 | Sudhir ...................... A61F 2/82 623/1.38 |
| 2013/0261736 A1 | 10/2013 | Kleiner et al. |
| 2013/0338762 A1 | 12/2013 | Jayasinghe et al. |
| 2014/0067044 A1 | 3/2014 | Trollsas et al. |
| 2014/0228932 A1 | 8/2014 | Rapoza |
| 2014/0343667 A1* | 11/2014 | McClain ................ A61L 31/148 623/1.38 |

OTHER PUBLICATIONS

Meille et al., Definitions of terms relating to crystalline polymers (IUPAC Recommendations 2011) Pure Appl. Chem. vol. 83, No. 10, pp. 1831-1871 (2011), (Aug. 3, 2011).

Van Vlack, "Elements of Materials Science and Engineering", University of Michigan, pp. 270-271, (1989), (Nov. 1, 1989).

LaDisa, Jr. et al., "Stent design properties and deployment ratio influence indexes of wall shear stress: a three-dimensional computational fluid dynamics investigation within a normal artery," J. Appl. Physicol., vol. 97, pp. 424-430, Jul. 2004.

* cited by examiner

HIGH MOLECULAR WEIGHT POLYLACTIDE AND POLYCAPROLACTONE COPOLYMER AND BLENDS FOR BIORESORBABLE VASCULAR SCAFFOLDS

BACKGROUND OF THE INVENTION

Field of the Invention

This invention relates polymeric medical devices, in particular, bioresorbable stents or stent scaffoldings Description of the State of the Art This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it possibly physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. A medicated stent may be fabricated by coating the surface of either a metallic or polymeric scaffold with a polymeric carrier that includes an active or bioactive agent or drug. Polymeric scaffolds may also serve as a carrier of an active agent or drug. An active agent or drug may also be included on a scaffold without being incorporated into a polymeric carrier.

Stents are generally made to withstand the structural loads, namely radial compressive forces, imposed on the scaffold as it supports the walls of a vessel. Therefore, a stent must possess adequate radial strength if its function is to support a vessel at an increased diameter. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading or pressure, which if exceeded, creates a yield stress condition resulting in the stent diameter not returning to its unloaded diameter, i.e., there is irrecoverable deformation of the stent. See, T. W. Duerig et al., Min Invas Ther & Allied Technol 2000: 9(3/4) 235-246. Stiffness is a measure of the elastic response of a device to an applied load and thus will reflect the effectiveness of the stent in resisting diameter loss due to vessel recoil and other mechanical events. Radial stiffness can be defined for a tubular device such as stent as the hoop force per unit length (of the device) required to elastically change its diameter. The inverse or reciprocal of radial stiffness may be referred to as the compliance. See, T. W. Duerig et al., Min Invas Ther & Allied Technol 2000: 9(3/4) 235-246.

When the radial yield strength is exceeded, the stent is expected to yield more severely and only a minimal force is required to cause major deformation. Radial strength is measured either by applying a compressive load to a stent between flat plates or by applying an inwardly-directed radial load to the stent.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erode or disintegrate through exposure to conditions within the body. Stents fabricated from biodegradable, bioabsorbable, bioresorbable, and/or bioerodable materials such as bioabsorbable polymers can be designed to completely erode only after the clinical need for them has ended.

In addition to high radial strength, a vascular scaffold must have sufficient resistance to fracture or sufficient toughness. A vascular scaffold is subjected to a large deformation during use, in particular, when it is crimped to a delivery diameter and when it is deployed. A scaffold may be susceptible to fracture when in use which can negatively impact performance and even lead to device failure. Fabricating a polymer-based scaffold that has sufficiently high radial strength as well as resistance to fracture is a challenge.

It is advantageous for vascular scaffolds to have thin struts while maintaining adequate radial strength. Thin struts lead to a lower profile device in the crimped state for better deliverability. After implantation, neointima proliferates until stent struts are covered. Consequently, thinner struts have less neointimal formation and less area obstruction of the vessel. Lastly, thin struts disturb blood flow less and are less thrombogenic. However, polymer based materials can be orders of magnitude lower in strength in terms of ultimate strength and stiffness compared to metallic alloys. Fabricating a polymer-based scaffold that has sufficiently high radial strength at strut thicknesses comparable to current metallic stents is therefore a challenge.

Additionally, treating peripheral vascular disease percutaneously in the lower limbs is a challenge with current technologies. Long term results are sub-optimal due to chronic injury caused by the constant motions of the vessel and the implant as part of everyday life situations. To reduce the chronic injury, a bioresorbable scaffold for the superficial femoral artery (SFA) and/or the popliteal artery can be used so that the scaffold disappears before it causes any significant long term damage. However, one of the challenges with the development of a femoral scaffold and especially a longer length scaffold (4-25 cm) to be exposed to the distal femoral artery and potentially the popliteal artery is the presence of fatigue motions that may lead to chronic recoil and strut fractures especially in the superficial femoral artery, prior to the intended bioresorption time especially when implanted in the superficial femoral artery.

Fabricating a polymer-based scaffold for treating the SFA is even more challenging than for coronary applications. A scaffold in the SFA and/or the popliteal artery is subjected to various non-pulsatile forces, such as radial compression, torsion, flexion, and axial extension and compression. These forces place a high demand on the scaffold mechanical performance and can make the scaffold more susceptible to fracture than less demanding anatomies. Stents or scaffolds for peripheral vessels such as the SFA, require a high degree of crush recovery. The term "crush recovery" is used to describe how the scaffold recovers from a pinch or crush load, while the term "crush resistance" is used to describe the force required to cause a permanent deformation of a scaffold. It has been believed that a requirement of a stent for SFA treatment is a radial strength high enough to maintain a vessel at an expanded diameter. A stent which combines such high radial strength, high crush recovery, and high resistance to fracture is a great challenge.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if each said individual publication, patent, or patent application was fully set forth, including any figures, herein.

SUMMARY OF THE INVENTION

A first set of embodiments of the present invention includes a stent comprising: a bioresorbable polymer scaffold comprising a polymer combination including a polylactide (PLA) polymer and polycaprolactone (PCL), wherein scaffold includes a plurality of interconnected struts and a thickness of the struts is less than 120 microns, wherein a number average molecular weight (Mn) of the polymer combination or a polymer of the polymer combination is greater than 110 kDa, and wherein the scaffold has a crimped state and a deployed state and a radial strength of the scaffold when expanded from the crimped state to the deployed state in saline or bodily fluid at 37° C. is at least 350 mm Hg.

The first set of embodiments may have one or more, or any combination of the following aspects (1) to (6): (1) wherein the polymer combination comprises a random copolymer of PLA and PCL random copolymer comprising a 1 to 5 mol % of caprolactone units; (2) wherein the polymer combination comprises a block copolymer of PLA polymer blocks and PCL polymer blocks including 1 to 5 wt % of PCL blocks; (3) wherein the polymer combination comprises a blend of a PLA homopolymer with PCL homopolymer; (4) wherein the PCL homopolymer is 1 to 5 wt % of the blend; (5) wherein the polymer combination comprises a blend of PLA polymer and a PLA and PCL copolymer; (6) wherein caprolactone units of the copolymer are 1 to 5 wt % of the blend.

A second set of embodiments of the present invention includes a stent comprising: a bioresorbable polymer scaffold comprising polymer formulation including a blend of PLA polymer and a PLA and PCL copolymer, wherein the scaffold includes a plurality of interconnected struts and a thickness of the struts is less than 120 microns, wherein a number average molecular weight (Mn) of the blend is greater than 60 kDa, and wherein the scaffold has a crimped state and a deployed state and a radial strength of the scaffold when expanded from the crimped state to the deployed state in saline or bodily fluid at 37° C. is at least 350 mm Hg.

The second set of embodiments may have one or more, or any combination of the following aspects (1) to (2): (1) wherein caprolactone units are 1 to 5 wt % of the formulation; (2) wherein the Mn of the blend is 100 to 250 kDa.

A third set of embodiments of the present invention includes a method of fabricating a stent including a bioresorbable scaffold, comprising: providing a polylactide (PLA) polymer resin having an intrinsic viscosity of 5 to 8 dL/g and a PLA and polycaprolactone (PCL) copolymer resin; forming a tube by melt processing the PLA resin and the copolymer comprising a blend of the PLA polymer and the copolymer; processing the formed tube to increase the crystallinity to at least 20%; and forming a scaffold from the processed tube comprising a plurality of struts having a thickness of less than 120 microns.

The third set of embodiments may have one or more, or any combination of the following aspects (1) to (3): (1) wherein the processing comprises radially expanding the formed tube to an expanded diameter and forming the scaffold from the tube at the expanded diameter; (2) wherein a percent radial expansion is at least 400%; (3) further comprising adding unreacted lactide monomer to the PLA polymer resin and the copolymer resin during the melt processing, wherein the scaffold comprises at least 0.5 wt % unreacted monomer content.

A fourth set of embodiments of the present invention includes a method of fabricating a stent including a bioresorbable scaffold, comprising: providing a tube comprising a blend of a PLA polymer and PLA and PCL copolymer formed from melt processing a PLA polymer resin having an intrinsic viscosity of 5 to 8 dL/g and a PLA/PCL copolymer resin; radially expanding the tube at least by 400%; and forming a scaffold from the expanded tube comprising a plurality of struts having a thickness of less than 120 microns, wherein the scaffold has a crimped state and a deployed state and a radial strength of the scaffold when expanded from the crimped state to the deployed state in saline or bodily fluid at 37° C. is at least 350 mm Hg.

The fourth set of embodiments may have one or more, or any combination of the following aspects (1) to (3): (1) wherein an Mn of the blend after sterilization of the scaffold is 100 kDa to 250 kDa; (2) wherein a size of a majority of the crystalline domains in the scaffold are 10 nm to 50 nm; (3) wherein a change in retardance as measured by polarized light microscopy (PLM) from an inner diameter to 50% of the thickness to the outer diameter of the scaffold is less than 50%.

DETAILED DESCRIPTION OF THE INVENTION

In many treatment applications using stents, stents expand and hold open narrowed portions of blood vessels. As indicated, to achieve this, the stent must possess a radial strength in an expanded state that is sufficiently high and sustainable to maintain the expanded vessel size for a period of weeks or months. This generally requires a high strength and rigid material. In the case of bioresorbable polymer stents or scaffolds, bioresorbable polymers that are stiff and rigid have been proposed and used in stents for coronary intervention. Such polymers are stiff or rigid under physiological conditions within a human body. These polymers tend to be semicrystalline polymers that have a glass transition temperature (Tg) in a dry state sufficiently above human body temperature (approximately 37° C.) that the polymer is stiff or rigid at these conditions. Polylactide and polylactide based polymers such as poly(L-lactide) are examples of such semicrystalline polymers that have been proposed and used as a stent or scaffold materials.

Fabricating a vascular scaffold from such materials with sufficient fracture toughness or fracture resistance is challenging due to their brittle nature. Vascular scaffolds are subjected to deformation and stress during manufacture when crimped to a delivery diameter, when deployed or expanded from a delivery diameter to a deployment diameter, and during use after deployment. As a result, vascular scaffolds are susceptible to fracture during manufacture (particularly during crimping), deployment, and use. The fracture toughness is important in reducing material-level damage during crimping and in vitro/in vivo deployment of a bioresorbable scaffold. The reduced damage allows achievement of a sufficiently high radial strength with a reduced strut thickness and cross-section.

It is a continuing challenge to develop new materials and processing methods for vascular scaffolds that improve the resistance to fracture with sufficiently high radial strength, particularly during crimping and deployment or expansion.

Another challenge in making a bioabsorbable polymer scaffold relates to the lower strength to weight ratio of polymers compared to metals. The strength of a scaffold material is proportional to the radial strength of the scaffold. Therefore, polymeric scaffolds require thicker struts than a metallic stent to achieve the radial strength required to provide patency to a blood vessel. Exemplary coronary polymer scaffolds have wall thicknesses from about 150 to 170 microns while coronary metallic stents have strut thicknesses of 60 to 100 microns. It is desirable to have a scaffold profile as low as possible. Thus, making a scaffold with a smaller form factor, i.e., with thinner struts, that provides sufficient radial strength is a challenge.

Figures 1A, 1B:
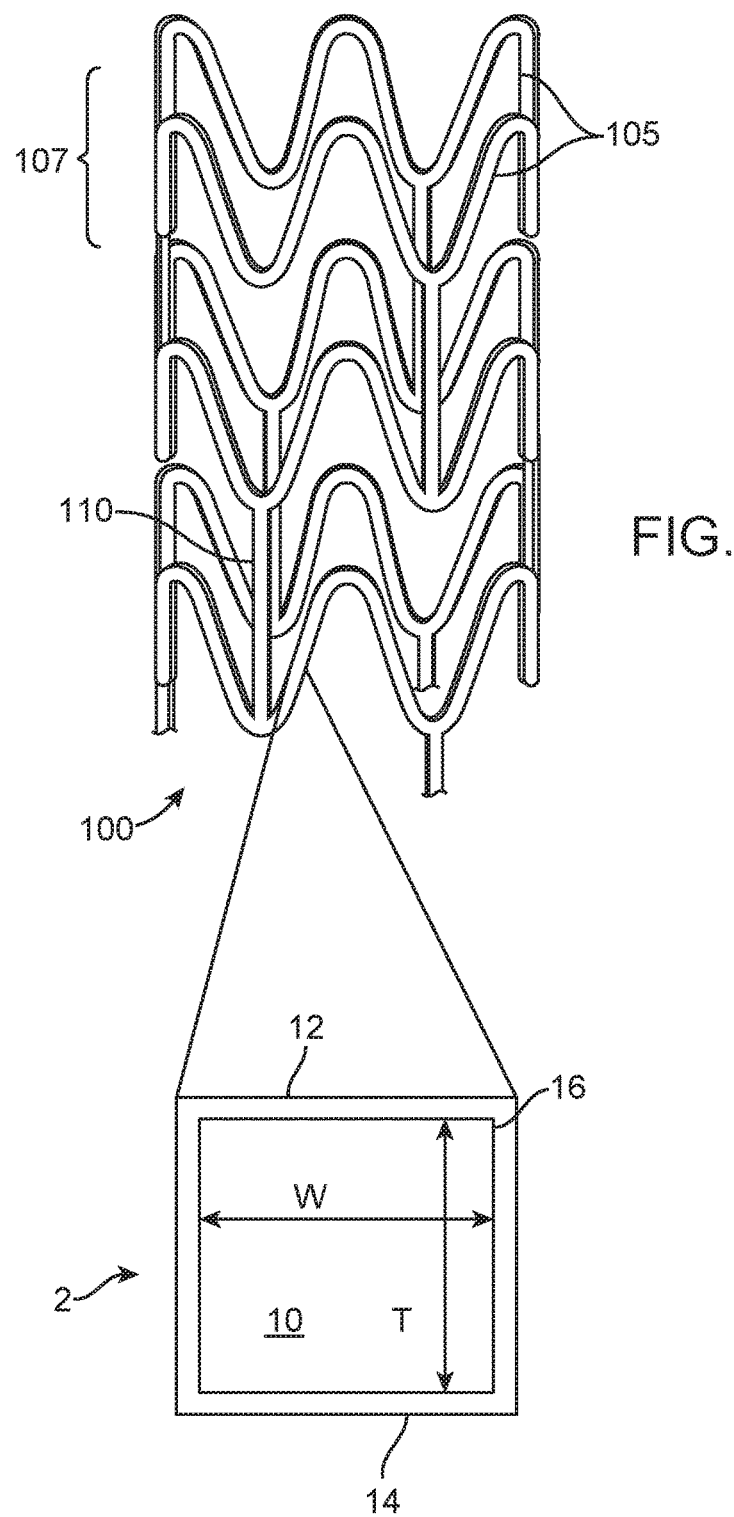
FIG. 1A depicts a view of an exemplary scaffold.
FIG. 1B show a cross-selection of a strut of the scaffold of FIG. 1A.

FIG. 1A depicts a view of an exemplary scaffold 100 which includes a pattern or network of interconnecting structural elements 105. FIG. 1A illustrates features that are typical to many stent patterns including cylindrical rings 107 connected by linking elements 110. The cylindrical rings are load bearing in that they provide radially directed force in response to an inward force on the scaffold. The linking elements generally function to hold the cylindrical rings together. Exemplary scaffolds are disclosed in US 2008/0275537, US 2011/0190872, and US 2011/0190871. Any of the patterns disclosed in these references are applicable to the inventive scaffolds.

FIG. 1B show a cross-selection of a strut 2 showing the polymer scaffold body, polymer backbone, or core of the strut surrounded by a drug/polymer coating or matrix 16. The cross-section of the strut has an abluminal or outer surface or side 12 that faces the vessel wall and a luminal or inner surface or side 14 that faces the lumen of the vessel. The strut cross-section shown is to be rectangular with a width (W) and thickness (T). The scaffold cross-section may be rectangular or approximately rectangular. The slight curvature at the inner and outer surfaces due to the tubular geometry is not shown. The present invention is not limited to this scaffold pattern or type of pattern and is applicable to any pattern.

Figure 2:
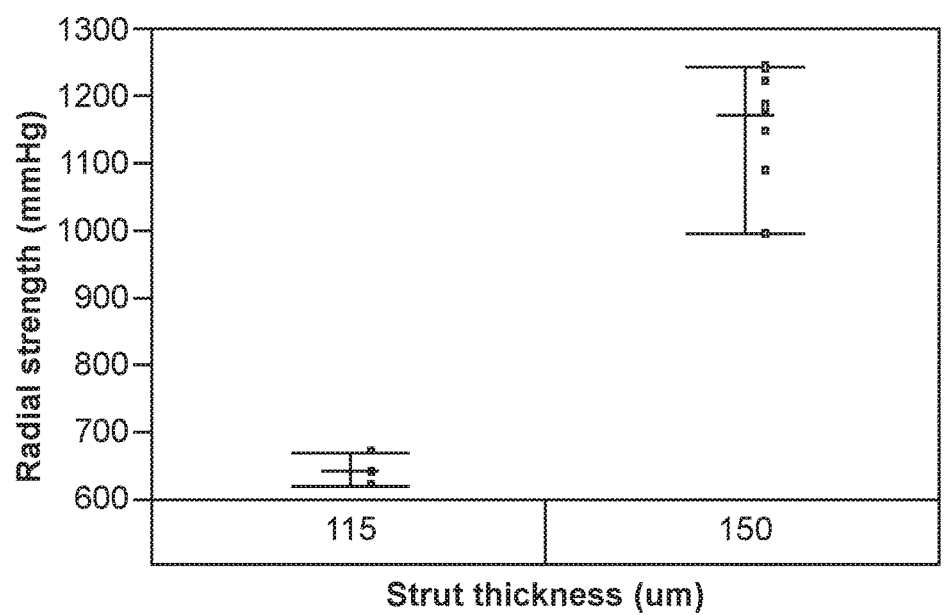
FIG. 2 depicts the radial strength dependence on strut thickness of a scaffold made from poly(L-lactide).

The challenge of obtaining a sufficiently high deployed scaffold radial strength for a polymer scaffold having significantly thinner struts than the 150 to 170 micron range is shown by FIG. 2. FIG. 2 depicts the radial strength dependence on strut thickness of a scaffold made from PLLA. The number average molecular weight (Mn) of the PLLA of the scaffold is less than 100 kg/mol. FIG. 2 shows the radial strength for two scaffolds of the same design with different strut thicknesses, 115 microns and 150 microns. The two scaffolds were in a crimped or reduced profile of about 0.055 in and then deployed in saline solution at 37° C. with a balloon to about 3.5 mm OD. The radial strength was measured by the MSI RX550 Radial Force Tester obtained from MSI of Flagstaff, Ariz. As shown, the scaffold with 150 micron thickness has a radial strength of about 1173 mm Hg and the scaffold with 115 micron thickness has a radial strength of about 650 mm Hg, showing the strong dependence of radial strength on dimensions.

In addition to resistance to fracture and reduced form factor, vascular scaffolds should possess degradation behavior that is favorable to treatment of vascular lesions. The degradation behavior refers to the temporal degradation profile of molecular weight, radial strength, and mass. Upon implantation, a bioresorbable scaffold should maintain its radial strength for a period of months to provide patency to the vessel while the vessel wall heals at the increased diameter. The desired minimum radial strength for coronary applications is 350 mm Hg. In addition, neointima grows over the scaffold which eventually covers all or most of the scaffold. After about three to six months the radial strength decreases significantly followed by breaking up of the scaffold and resorption of the scaffold material. This allows the vessel to regain a healthy unrestricted natural state which includes further expansion and resumption of vasomotion. The scaffold should completely resorb from the vessel within 18 to 36 months.

Embodiments of the present invention are directed to implantable medical devices such as bioresorbable vascular scaffolds including a high molecular weight polymer having thin struts in a selected range and sufficient radial strength to support a vessel upon deployment. The inventive scaffolds may further have degradation behavior of molecular weight, radial strength, and mass that are conducive to healing of a vessel, as described herein, including providing patency to a vessel, reduction of radial strength, breaking up, and resorbing to allow return of the vessel to a natural state.

Selected ranges of strut thickness include less than 150 microns, less than 140 microns, less than 130 microns, about 100 micron, 80 to 100 microns, 80 to 120 microns, 90 to 100 microns, 90 to 110 microns, 110 to 120 microns, or 95 to 105 microns. The thickness may refer to a thickness of a scaffold that is formed by laser cutting a tube. The thickness may further refer to the thickness of the scaffold formed from laser cutting plus a thickness of a coating over the laser cut scaffold. All or a majority of the struts of the scaffold may have a thickness in the selected range. An aspect ratio of strut width divided by strut thickness may be defined. Selected ranges of this aspect ratio include less than 3, less than 2, less than 1, less than 0.5, 0.75 to 2, or 0.9 to 1.5.

The radial strength of the scaffold can be high enough to provide mechanical support to a vessel after expanding the vessel to an increased diameter or prevent or reduce a decrease in the diameter of the vessel. The scaffold has a crimped state and a deployed state and a radial strength of the scaffold may refer to a radial strength when expanded from the crimped state to the deployed state in saline or bodily fluid at 37° C. The radial strength may be at least the value required to support a vessel at a reference vessel diameter, which is the healthy diameter of a vessel at an implant site. The radial strength is at least 350 mm Hg, at least 500 mm Hg, at least 650 mm Hg, at least 800 mm Hg, at least 1000 mm Hg, 400 to 600 mm Hg, 500 to 1200 mm Hg, 700 to 900 mm Hg, or 800 to 1300 mm Hg.

The high molecular weight polymer, the polymer formulation of the scaffold, and processing to modify morphology combine to provide sufficiently high radial strength for the thin strut scaffold. The vascular devices may further be resistant to fracture when crimped to a reduced diameter and when expanded to a deployment diameter, which also helps provide the high radial strength. The polymer formulation includes a polylactide polymer component and a polycaprolactone component as a homopolymer, blocks, or as part of a random copolymer. The high molecular weight is provided by starting with a polymer resin having an intrinsic viscosity (IV) of 4 to 8 dL/g and processing that results in a finished product number average molecular weight (Mn) of 70 to 250 kDa or 100 to 250 kDa. Finished product may refer to the stent after sterilization.

The degradation behavior may be characterized in terms of the time dependent molecular weight. The molecular weight (Mn) of the high molecular weight polymer may be less than 100 kDa, 90 kDa, 80 kDa, 70 kDa, 60 kDa, 60 to 100 kDa, 60 to 80 kDa, or 80 to 100 kDa at 1 year of exposure of the scaffold to saline or bodily fluids at 37° C.

Embodiments of the inventive scaffold having features described above include a scaffold material including formulations or combinations of polylactide (PLA) polymers and polycaprolactone. A polylactide polymer is one which contains L-lactide or L-lactic acid in the polymer backbone and may optionally have other bioresorbable monomers. The polymer combination includes a polymer having a high molecular, as defined herein. The polycaprolactone component and the high molecular weight help provide sufficient radial strength and high fracture toughness of the scaffold.

The polymer combinations can include a blend, a random copolymer, or a block copolymer, of a PLA polymer and polycaprolactone (PCL). The stent body, scaffold, or substrate made partially or completely made of polymer combination. The stent body may also include a coating that includes a therapeutic agent.

The polymer combinations include: (1) PLA and PCL random copolymer; (2) block copolymer including PLA polymer blocks and PCL polymer blocks; (3) a blend of a PLA polymer with PCL homopolymer; (4) blend of a PLA homopolymer blended and a PLA and PCL copolymer; and (5) a blend of a PCL homopolymer and a PLA and PCL copolymer.

Embodiments of the invention include a scaffold made substantially or completely of the polymer combination. "Substantially" may correspondent to greater than 90 wt %, greater than 95 wt %, or greater than 99 wt %. The scaffold may have a composition of 90 to 95% or 95 to 99% of the polymer combination. The scaffold may include other components that include, but are not limited to, fillers, plasticizers, visualization materials (e.g., radiopaque), or therapeutic agents.

The PLA polymer of the combination may include poly(L-lactide) (PLLA), poly(D,L-lactide) having a constitutional unit weight-to-weight (wt/wt) ratio of about 96/4, poly(lactide-co-glycolide), poly(L-lactide-co-glycolide), poly(D,L-lactide-co-glycolide), poly(D,L-lactide) made from meso-lactide, and poly(D,L-lactide) made from polymerization of a racemic mixture of L- and D-lactides. A PLA polymer can include a PLA with a D-lactide content greater than 0 mol % and less than 15 mol %, or more narrowly, 1 to 15 mol %, 1 to 5 mol %, 5 to 10%, or 10 to 15 mol %. The PLA polymer includes poly(D,L-lactide) having a constitutional unit weight-to-weight (wt/wt) ratio of about 93/7, about 94/6, about 95/5, about 96/4, about 97/3, about 98/2, or about 99/1. The term "unit" or "constitutional unit" refers to the composition of a monomer as it appears in a polymer.

Embodiments of the invention include a scaffold including a PLA and PCL random copolymer. The scaffold may be made substantially or completely of the copolymer. The copolymer may include poly(L-lactide-co-caprolactone), poly(D,L-lactide-co-caprolactone), poly(L-lactide-co-glycolide-co-caprolactone), and poly(DL-lactide-co-glycolide-co-caprolactone). The copolymer with D,L-lactide may be made from a racemic mixture of L- and D-lactide or may include 1 to 15% of D constitutional units. The scaffold may be made substantially or completely of the copolymer. In some embodiments, the scaffold may include no PLA homopolymer, PCL homopolymer, or less than 20%, 10%, 5%, or less than 1% of either homopolymer.

The copolymer may include 1 to 5% (wt % or mol %) of caprolactone units, or more narrowly, 1 to 2%, 2 to 5%, 3 to 5%, or about 3%. The scaffold may be made from a copolymer resin with an IV greater than 5 dL/g, greater than 7 dL/g greater than 8 dl/g, 3.8 to 8 Dl/g, 4 to 8 dL/g, 4 to 6 dL/g, 6 to 8 dL/g, or 5 to 7 dL/g. The Mn of the copolymer in a finished scaffold may be 100 to 250 kDa.

The Tm of copolymer resin or copolymer of the scaffold may be 165° C. The Tg of the copolymer may be 60 to 65° C.

The crystallinity of the copolymer or scaffold made of the copolymer may be 20 to 50%, 20 to 25%, 25 to 30%, 30 to 35%, 35 to 40%, 40 to 45%, and 45 to 50%.

Embodiments of the invention include a scaffold including a block copolymer including PLA polymer blocks and PCL polymer blocks. The scaffold may be made substantially or completely of the block copolymer. The block copolymer may be a linear block copolymer or branched block copolymer such as a star block copolymer.

The scaffold may include no PLA homopolymer, PCL homopolymer, or less than 20%, 10%, 5%, or less than 1% of either homopolymer. The PLA blocks may include PLLA, poly(L-lactide-co-glycolide), poly(D,L-lactide-co-glycolide), and poly(D,L-lactide). Blocks with D,L-lactide may be made from a racemic mixture of L- and D-lactide or may include 1 to 15% of D constitutional units. The scaffold may be made substantially or completely of the block copolymer.

The block copolymer may include 1 to 5% (wt % or mol %) of polycaprolactone blocks, or more narrowly, 1 to 2%, 2 to 5%, 3 to 5%, or about 3%. The scaffold may be made from a copolymer resin with an IV greater than 5 dL/g, greater than 7 dL/g greater than 8 dl/g, 4 to 8 dL/g, 4 to 6 dL/g, 6 to 8 dL/g, or 5 to 7 dL/g. The Mn of the block copolymer in a finished scaffold may be 100 to 250 kDa.

The Tm of copolymer resin or copolymer of the scaffold may be 60 and 150 to 185° C. for PCL and PLA block, respectively. The Tg of the copolymer may be −60 and 60 to 75° C. for PCL and PLA block, respectively. The crystallinity of the copolymer or scaffold made of the copolymer may be 20 to 50%, 20 to 25%, 25 to 30%, 30 to 35%, 35 to 40%, 40 to 45%, and 45 to 50%.

Embodiments of the invention include a scaffold including a blend of a PLA polymer with a PCL homopolymer. The scaffold may be made substantially or completely of the blend. The PLA polymer may include PLLA, poly(L-lactide-co-glycolide), poly(D,L-lactide-co-glycolide), and poly(D,L-lactide). PLA polymers with D,L-lactide may be made from a racemic mixture of L- and D-lactide or may include 1 to 15% of D constitutional units. The scaffold may be made substantially or completely of the block copolymer.

The blend may include 1 to 5% (wt % or mol %) of PCL homopolymer, or more narrowly, 1 to 2%, 2 to 5%, 3 to 5%, or about 3%. The scaffold may be made from a PLA resin or resin blend with an IV greater than 5 dL/g, greater than 7 dL/g greater than 8 dl/g, 4 to 8 dL/g, 4 to 6 dL/g, 6 to 8 dL/g, or 5 to 7 dL/g.

The Mn of the blend in the finished scaffold may be 100 to 250 kDa.

The Tm of the blend may be 150 to 185° C. There may or may not be a Tm of 60° C. that is attributed to the PCL homopolymer. The Tg of the blend may be 60 to 75° C. There may or may not be a Tg of −60° C. that is attributed to the PCL homopolymer.

The crystallinity of the blend or scaffold made of the blend may be 20 to 50%, 20 to 25%, 25 to 30%, 30 to 35%, 35 to 40%, 40 to 45%, and 45 to 50%.

Embodiments of the invention include a scaffold including a blend of a PLA polymer with a PLA and PCL copolymer. The scaffold may be made substantially or completely of the blend. The PLA polymer may include PLLA, poly(L-lactide-co-glycolide), poly(D,L-lactide-co-glycolide), and poly(D,L-lactide). PLA polymers with D,L-lactide may be made from a racemic mixture of L- and D-lactide or may include 1 to 15% of D constitutional units.

The copolymer may be PLA and PCL random copolymer or a block copolymer of PLA polymer blocks and PCL homopolymer blocks. The random copolymer may include any from the list of PLA and PCL random copolymers provided above. The block copolymer may be linear block copolymer or branched block copolymer such as a star block copolymer. The scaffold may be made substantially or completely of the blend.

The scaffold may be made from a PLA resin or the resin blend with an IV greater than 5 dL/g, greater than 7 dL/g greater than 8 dl/g, 4 to 8 dL/g, 4 to 6 dL/g, 6 to 8 dL/g, or 5 to 7 dL/g. The Mn of the PLA polymer in a finished scaffold may be 150 to 300 kDa. The Mn of the copolymer in a finished scaffold may be 100 to 250 kDa. The Mn of the blend in the finished scaffold may be 100 to 250 kDa.

The caprolactone units in either the random or block copolymer may be 1 to 5% (wt % or mol %) of the blend, or more narrowly, 1 to 2%, 2 to 5%, 3 to 5%, or about 3% of the blend. The random copolymer may be 1% to 50% caprolactone units. Exemplary random copolymers include 95/5 poly(L-lactide-co-caprolactone), wherein 95/5 refers to 95 mol % L-lactide and 5% caprolactone, and 70/30 poly(L-lactide-co-caprolactone), wherein 70/30 refers to 70 mol % L-lactide and 30 mol % caprolactone. The IV of the copolymer resin used may be 1.5 g/dL, 3.8 g/dL, or higher.

The Tm of the blend may be 160 to 185° C. The Tg of the blend may be 60 to 75° C., and greater than 37° C. when hydrated.

The crystallinity of the blend or scaffold made of the blend may be 20 to 50%, 20 to 25%, 25 to 30%, 30 to 35%, 35 to 40%, 40 to 45%, and 45 to 50%.

Embodiments of the invention include a scaffold including a blend of a PCL homopolymer with a PLA and PCL copolymer. The scaffold may be made substantially or completely of the blend. The copolymer may be PLA and PCL random copolymer or a block copolymer of PLA polymer blocks and PCL homopolymer blocks. The random copolymer may include any from the list of PLA and PCL random copolymers provided above. The block copolymer may include any from the list of PLA and PCL block copolymers provided above. The block copolymer may be linear block copolymer or branched block copolymer such as a star block copolymer. The scaffold may be made substantially or completely of the blend.

The scaffold may be made from a copolymer resin or the resin blend with an IV greater than 5 dL/g, greater than 7 dL/g greater than 8 dl/g, 4 to 8 dL/g, 4 to 6 dL/g, 6 to 8 dL/g, or 5 to 7 dL/g. The Mn of the blend polymer in a finished scaffold may be 100 to 250 kDa. The total caprolactone units in both the copolymer and the PCL may be 1 to 5% (wt % or mol %) of the blend, or more narrowly, 1 to 2%, 2 to 5%, 3 to 5%, or about 3% of the blend. The PCL homopolymer may be 0.5% to 4% of the blend. The caprolactone content of the copolymer may be 0.5% to 4%.

Exemplary random copolymers include 95/5 poly(L-lactide-co-caprolactone), wherein 95/5 refers to 95 mol % L-lactide and 5% caprolactone and 70/30 poly(L-lactide-co-caprolactone), where 70/30 refers to 70 mol % L-lactide and 30% caprolactone. The IV of the copolymer resin used may be 1.5 dL/g, 3.8 dL/g, or higher.

The Tm of the blend may be 160 to 185° C. The Tg of the blend may be 60 to 75° C.

The crystallinity of the blend or scaffold made of the blend may be 20 to 50%, 20 to 25%, 25 to 30%, 30 to 35%, 35 to 40%, 40 to 45%, and 45 to 50%.

The inventive scaffolds may further have degradation behavior of molecular weight, radial strength, and mass that are conducive to and promote healing of a vessel, as described herein. The higher molecular weight of the inventive scaffolds, as compared to scaffolds with Mn less than about 100 kDa, will result in degradation times of molecular weight, radial strength and mass that are the same or not significantly higher. It has been reported in the literature that in PLLA/PCL combinations, the PCL accelerates degradation, as compared to PLLA without PCL. For example, Tsuji, H. et al., Journal of Applied Polymer Science 67, 405-415 (1998) have reported that adding PCL into PLLA system accelerates degradation as long as the PCL molecular weight is lower than that of PLLA and the amount of PCL is less than 50%. In the present invention, the Mn of the PCL in blends of PLLA and PCL is less than the Mn of PLLA.

It has also been shown that adding PCL to a PLLA system accelerates degradation as long as the following conditions are met: 1) the PCL molecular weight is lower than that of PLLA and 2) the amount of PCL is less than 50%. (Tsuji, H., Ikada, Y, Journal of Applied Polymer Science 67, 405-415 (1998)) It has also been shown that a PLLA/PCL 95/5 copolymer degrades twice as fast as PLLA.

Therefore, utilizing a PLLA/PCL resin with an IV of 5 to 7 dL/g will not cause a significantly slower degradation rate compared to a PLLA scaffold made from a resin with an IV of 3.8 dL/g or less.

Thus, in general, the molecular weight and amount of PCL can be adjusted to obtain the degradation properties disclosed herein.

Figure 3:
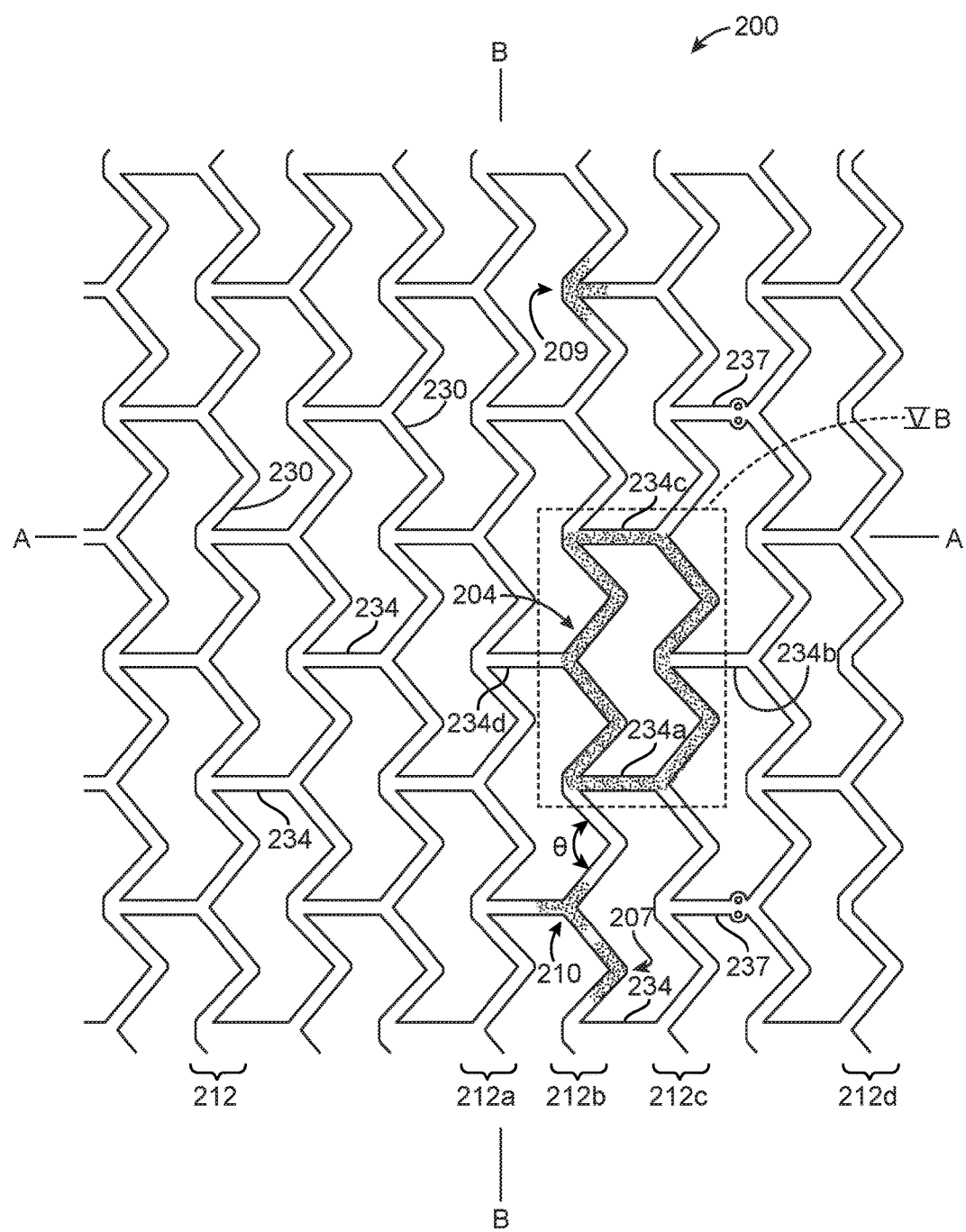
FIG. 3 depicts an embodiment of a scaffold pattern.

The scaffold materials disclosed may be used with a variety of scaffold patterns. FIG. 3 depicts a first embodiment of a pattern 200 which includes longitudinally-spaced rings 212 formed by struts 230. The pattern 200 of FIG. 3, represents a tubular scaffold structure (for example, as shown in FIG. 1), so that an axis A-A is parallel to the central or longitudinal axis of the scaffold. The scaffold structures shown may be in a state prior to crimping or after deployment.

In FIG. 3, a ring 212 is connected to an adjacent ring by several links 234, each of which extends parallel to axis A-A. In this first embodiment of a scaffold pattern (pattern 200) four links 234 connect the interior ring 212, which refers to a ring having a ring to its left and right in FIG. 3, to each of the two adjacent rings. Thus, ring 212*b* is connected by four links 234 to ring 212*c* and four links 234 to ring 212*a*. Ring 212*d* is an end ring connected to only the ring to its left in FIG. 3. The rings are undulating and may be approximately zig-zag or sinusoidal in shape.

A ring 212 is formed by struts 230 connected at crowns 207, 209 and 210. A link 234 is joined with struts 230 at a crown 209 (W-crown) and at a crown 210 (Y-crown). A crown 207 (free-crown) does not have a link 234 connected to it. A "W-crown" refers to a crown where the angle extending between a strut 230 and the link 234 at the crown 210 is an obtuse angle (greater than 90 degrees). A "Y-crown" refers to a crown where the angle extending between a strut 230 and the link 234 at the crown 209 is an acute angle (less than 90 degrees). The same definitions for Y-crown and W-crown also apply to the cell 304 below.

Preferably the struts 230 that extend from a crown 207, 209 and 210 at a constant angle from the crown center, i.e., the rings 212 are approximately zig-zag in shape, as opposed to sinusoidal for pattern 200, although in other embodiments a ring having curved struts is contemplated.

As such, in this embodiment a ring 212 height, which is the longitudinal distance between adjacent crowns 207 and 209/210 may be derived from the lengths of the two struts 230 connecting at the crown and a crown angle θ. In some embodiments the angle θ at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 3). The struts 212 centroidal axes lie primarily at about the same radial distance from the scaffold's longitudinal axis. Ideally, substantially all relative movement among struts forming rings also occurs axially, but not radially, during crimping and deployment. Although, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the tube from which the scaffold is cut) is always greater than a maximum expanded scaffold diameter that the delivery balloon can, or is capable of producing when inflated. According to one embodiment, a pre-crimp diameter is greater than the scaffold expanded diameter, even when the delivery balloon is hyper-inflated, or inflated beyond its maximum use diameter for the balloon-catheter.

Pattern 200 includes four links 237 (two at each end, only one end shown in FIG. 3) having structure formed to receive a radiopaque material in each of a pair of transversely-spaced holes formed by the link 237. These links are constructed in such a manner as to avoid interfering with the folding of struts over the link during crimping, which, as explained in greater detail below, is necessary for a scaffold capable of being crimped to a diameter of about at most Dmin or for a scaffold that when crimped has virtually no space available for a radiopaque marker-holding structure.

Links 234*b* and 234*d* connect the cell 204 to the right and left adjacent rings in FIG. 3, respectively. Link 234*b* connects to cell 204 at a W-crown 209. Link 234*d* connects to cell 04 at a Y-crown 210. There are four crowns 207 for cell 204, which may be understood as four crowns devoid of a link 234 connected at the crown. There is only one free crown between each Y-crown and W-crown for the cell 204. Cell 204 may be referred to as a W closed cell element since its shape resembles the letter "W", for example, cell 204 shown by box VB.

There are four cells 204 formed by each pair of rings 212 in pattern 200, e.g., four cells 204 are formed by rings 212*b* and 212*c* and the links 234 connecting this ring pair, another four cells 204 are formed by rings 212*a* and 212*b* and the links connecting this ring pair, etc. Cell 204 may be referred to as a W closed cell element since its shape resembles the letter "W", for example, cell 204 shown by box VB.

Figure 4:
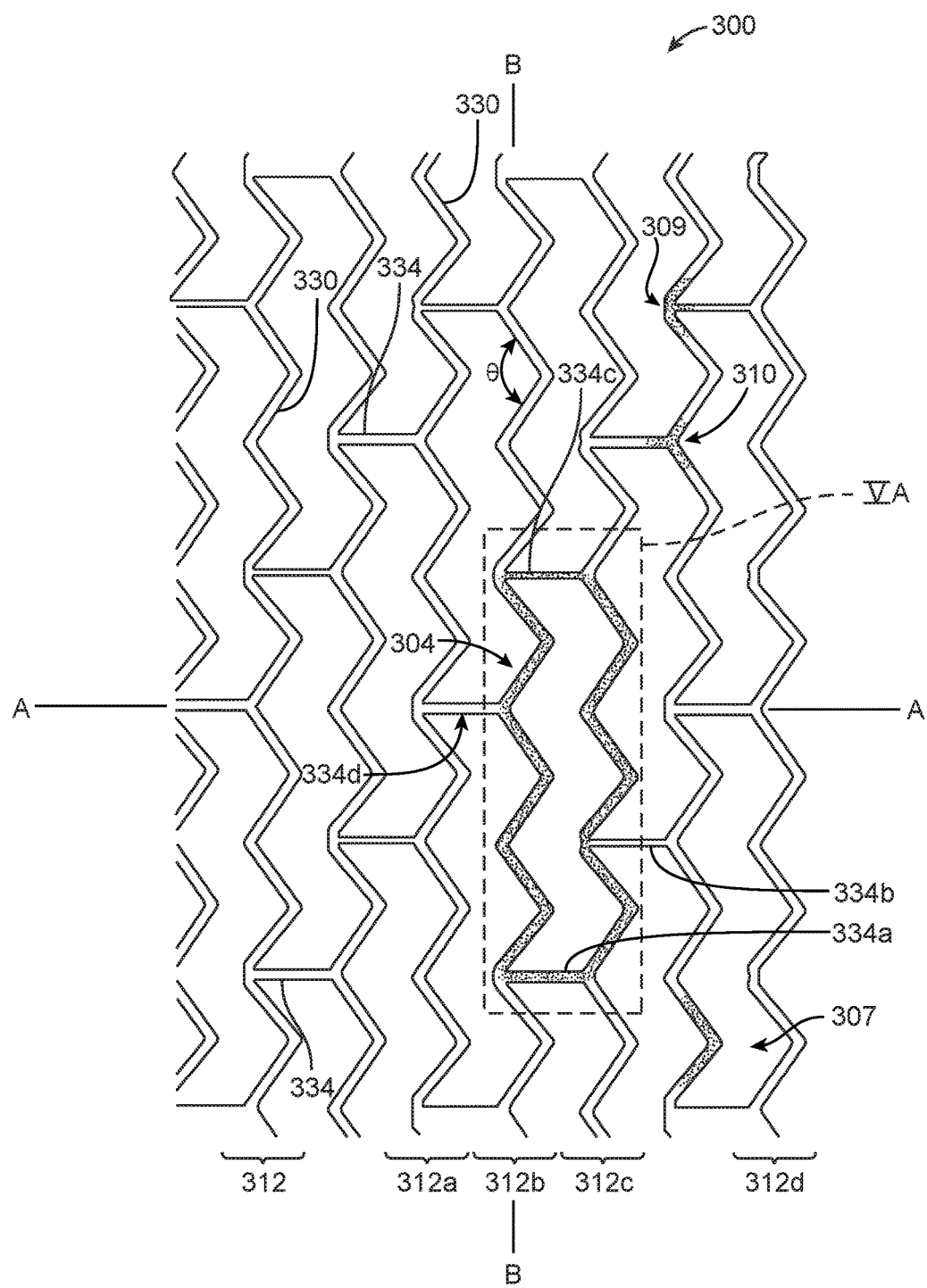
FIG. 4 depicts another embodiment of a scaffold pattern.

FIG. 4 depicts another embodiment of a scaffold pattern 300. Like the pattern 200, the pattern 300 includes longitudinally-spaced rings 312 formed by struts 330. A ring 312 is connected to an adjacent ring by several links 334, each of which extends parallel to axis A-A. The description of the structure associated with rings 212, struts 230, links 234, and crowns 207, 209, 210 in connection with FIG. 3, above, also applies to the respective rings 312, struts 330, links 334 and crowns 307, 309 and 310 of the second embodiment, except that in the second embodiment there are only three struts 334 connecting each adjacent pair of rings, rather than four. Thus, in the second embodiment the ring 312*b* is connected to the ring 312*c* by only three links 334 and to the ring 312*a* by only three links 334. A link formed to receive a radiopaque marker, similar to link 237, may be included between 312*c* and ring 312*d*. In contrast to pattern 200, there are three cells 304 formed by a ring pair and their connecting links in pattern 300.

Links 334*b* and 334*d* connect the cell 304 to the right and left adjacent ring in FIG. 4, respectively. Link 334*b* connects to cell 304 at a W-crown 309. Link 334*d* connects to cell 304 at a Y-crown 310. There are eight connected or free crowns 307 for cell 304, which may be understood as eight crowns devoid of a link 334 connected at the crown. There are one or three free crowns between a Y-crown and W-crown for the cell 304. Cell 304 may be thought of as a W-V closed cell element since its shape resembles the letters "W" and "V", for example, cell 304 shown by box VA.

Comparing FIGS. 3 to 4, one can appreciate that the W cell 204 is symmetric about the axes B-B and A-A whereas the W-V cell 304 is asymmetric about both of these axes. The W cell 204 is characterized as having no more than one crown 207 between links 234. Thus, a Y-crown crown or W-crown is always between each crown 207 for each closed cell of pattern 200. In this sense, pattern 200 may be understood as having repeating closed cell patterns, each having no more than one crown that is not supported by a link 234. In contrast, the W-V cell 304 has three unsupported crowns 307 between a W-crown and a Y-crown. As can be appreciated from FIG. 4A, there are three unsupported crowns 307 to the left of link 334d and three unsupported crowns 307 to the right of link 334b.

Another embodiment of a pattern includes a repeating pattern of W-W cells. The sequence of crests starting at a W-crown and going around a circumference of a ring is: W-crown, 3-free crowns, Y-crown, 2 free crowns, W-crown, etc. Thus, there are either 2 or 3 free crowns between a W-crown and Y-crown.

Crown angle θ in any of the patterns may be greater than 70°, greater than 80°, greater than 90°, greater than 100°, 70° to 80°, 80° to 90°, 90° to 100°, 100° to 120°, 100° to 130°, 120° to 130°, 120° to 140°, or 130° to 140°.

The fabrication of the inventive scaffold may include the following processes or steps: forming a hollow, thin-walled polymeric tube (i.e., pre-cut tube), preferably with no holes in the walls; processing that increases the strength of the polymer of the scaffold body and also the radial strength of the scaffold; forming a stent scaffolding made up of thin struts from the tube by laser machining a stent pattern in the tube; optionally forming a therapeutic coating over the scaffolding; crimping the scaffold over a delivery balloon, and sterilization of the scaffold using radiation, an ethylene oxide process, or some other sterilization process. Detailed discussion of the manufacturing processes of a bioabsorbable stent can be found elsewhere, e.g., U.S. Patent Publication Nos. 2007/0283552 and 2012/0073733.

A pre-cut tube can be formed by a melt processing method such as extrusion or injection molding. In extrusion, for example, a polymer resin is fed into an extruder inlet and conveyed through the extruder barrel as a melt above the melting temperature (Tm) of the polymer. For example, the temperature of the melt in the extruder may be 180 to 250° C. At the end of the extruder barrel, the polymer melt is forced through a die to form a tubular film which is longitudinaly drawn and cooled to form the tube.

The degree of crystallinity of the tube formed from the melt processing may be 0%, less than 5%, less than 10%, 5 to 10%, or 10 to 15%.

A polymer resin is the raw material used for the melt processing for forming the polymeric tube. In order to provide the high molecular weight of the finished sterilized product, the resin has a much higher molecular weight than the finished product. The molecular weight of the resin may be expressed in terms of the intrinsic viscosity (IV) in dL/g. The IV of a polymer resin may be higher than 5 dL/g, greater than 7 dL/g greater than 8 dl/g, 4 to 8 dL/g, 5 to 8 dL/g, 4 to 6 dL/g, 6 to 8 dL/g, or 5 to 7 dL/g.

The polymer of inventive scaffold after sterilization has a number average molecular weight (Mn) of 100 to 250 kDa. The molecular weight of the polymer decreases during the processing steps. Most of the decrease occurs during the melt processing of the resin and during sterilization if radiation sterilization is used.

In addition to the type of polymer(s) and their relative composition, the strength of the scaffold material and the radial strength the scaffold also depend on the morphology of the scaffold polymer. Morphology includes crystallinity, crystal domain size, and polymer chain alignment in crystalline and amorphous domains. Thus, the strength and radial strength can further be modified by additional processing that modifies the morphology of the polymer, which increases the strength of the scaffold material and the radial strength of the scaffold.

The additional processing may increase the crystallinity of the scaffold material which increases the strength and stiffness of the scaffold material and the radial strength and radial stiffness of the scaffold. Additional processing may also be performed that increases the alignment of the scaffold polymer chains in the circumferential or hoop direction, axial direction, or both which increases the strength of the scaffold material and radial strength of the scaffold. The processing can be performed prior to laser cutting, after laser cutting, or both. Preferably, the processing is performed prior to laser cutting.

The additional processing can include annealing the pre-cut tube and/or the scaffold at a temperature and for a time sufficient to increase the crystallinity to a desired level. The annealing can be performed prior to laser cutting, after laser cutting, or both. Preferably, the processing is performed prior to laser cutting. The temperature may be between the glass transition temperature (Tg) of the scaffold polymer and the melting temperature (Tm) of the scaffold polymer. The annealing process can include heating and maintaining a polymer construct in a temperature range for a selected period of time. The annealing process may increase the crystallinity from the initial crystallinity to 20 to 30%, 20 to 25%, 30 to 40%, 40 to 45%, 45 to 50%, and greater than 50%. The annealing temperature may be any temperature between the Tg to the Tm of the polymer or a polymer of the scaffold. More narrowly, the temperature may be Tg+5° C., Tg+5° C. to Tg+10° C., Tg+10° C. to Tg+15° C., Tg+15° C. to Tg+20° C., Tg+20° C. to Tg+25° C., Tg+25° C. to Tg+30° C., or greater than Tg+30° C. The annealing time may be 1 min to 10 days, or more narrowly, 1 min to 30 min, 30 min to 1 hr, 1 hr to 3 hr, 3 hr to 10 hr, 10 hr to 1 day, 1 day to 5 days, or 5 to 10 days.

Additionally or alternatively, the processing can include radially deforming the pre-cut tube to increase the radial strength of the tube. The radially expanded tube may then be laser cut to form a scaffold. The radial expansion increases the radial strength both through an increase in crystallinity and induced polymer chain and crystal alignment in the circumferential or hoop direction. The radial expansion process may be performed by several processes including blow molding (e.g., US 2011/0066222) or by expanding over a mandrel (e.g., WO 2014/045068). In blow molding, the pre-cut tube is disposed within a mold and heated to a temperature between Tg and Tm and expanded by increasing a pressure inside of the tube.

In embodiments of additional processing without radial expansion, a tube may be formed by melt processing having a target thin scaffold thickness. The formed tube may also have a target diameter of a finished scaffold or target scaffold diameter. The tube may then be annealed to increase the crystallinity to a desired level, as disclosed herein. In some embodiments, the tube may be annealed at a fixed diameter which may be performed by annealing over a tubular mandrel having an outside diameter the same as the inside diameter of the scaffold or outside diameter slightly smaller to allow a friction fit of the tube over the mandrel. Alternatively, the formed tube may have a diameter larger than the target scaffold diameter, for example, 1 to 10%, or more narrowly, 5 to 10% larger. The formed tube may then be annealed over a mandrel having an outside diameter equal to the target diameter of the finished scaffold. The formed tube may then be shrunk to fit over the mandrel when annealed so that it has the target scaffold diameter after the annealing. After any of these annealing alternatives, the annealed scaffold may then be cut to form the scaffold.

In embodiments of additional processing including radial expansion, a tube may be formed by melt processing having a formed tube thickness greater than the target thin scaffold thickness and a tube diameter less than the target scaffold diameter. In such embodiments, the formed tube may be radially expanded so that the radially expanded tube has the target scaffold diameter and the target thin scaffold thickness. The tube may also be axially elongated during the radial expansion. The radially expanded tube may then be cut to form the scaffold.

The degree of radial expansion may be quantified by the radial expansion ratio (RE ratio): $ID_{expanded}/ID_{initial}$ or the percent expansion (% RE)=(RE ratio−1)×100%. The % RE may be 200 to 400%, 400 to 500%, 500 to 550%, 550 to 600%, or greater than 500%. Similarly, the degree of axial elongation, may be quantified by an axial elongation (AE) ratio, $L_{elongated}/L_{original}$ or the percent Axial extension (% AE)=(AE ratio−1)×100%. The % AE may be 20% to 50%, 50% to 100%, 100% to 200%, or greater than 200%.

Exemplary embodiments include a formed tube with a thickness of 75 microns to 150 microns and outer diameter of 2 mm to 5.0 mm.

In alternative embodiments, the formed tube may be radially expanded so that the radially expanded tube has the target thin scaffold thickness, but with a diameter slightly larger (e.g., 1 to 10% larger) than the target scaffold diameter. The radially expanded tube may then be annealed, as described above, to shrink fit the tube over a mandrel so that the annealed radially expanded tube has the target scaffold diameter.

The size of the crystalline domains may also influence the properties of the polymer and scaffold. It has been found that a larger number of smaller crystalline domains improve fracture toughness and thus improve radial strength. The temperature of the additional processing that increases crystallinity (annealing, radial expansion) influences the size of the crystalline domains generated. It has found that lower temperatures closer to Tg favor smaller crystalline domains, for example, Tg to Tg+30 or Tg+10 to Tg+30. The scaffold may include crystalline domain sizes of less than 10 nm, 10 nm to 50 nm, 10 to 20 nm, 10 to 30 nm, 20 to 40 nm, 40 to 50 nm, or greater than 50 nm. The disclosed range may correspond to the average crystalline domain size or a majority of the crystalline domain sizes.

It is believed that the high molecular weight of the polymer tube may provide improved polymer orientation from radial expansion, and thus, improved radial strength over a thicker target tube thickness. The inventors have found that radial expansion of lower molecular weight PLLA tubes made from a resin of 3.8 dL/g, an orientation gradient results between the inside diameter (ID) and the outside diameter (OD) of the expanded tubes and scaffolds made from the tubes. The tubes were expanded using blow molding. The scaffold after sterilization had an Mn of 70 to 100 kDa. The tubes had an initial wall thickness of 0.0215 in and were expanded 400% from an outer diameter of 0.068 in to an outer diameter of 0.1365 in with a thickness of about 0.0062 inches.

Studies using polarized light microcopy (PLM) of a radial section of the scaffold have shown that the degree of orientation of polymer chains or crystals decreases between the ID and the OD of the scaffold. Polarized light microscopy refers to optical microscopy techniques involving illumination of sample with polarized light. PLM is most commonly used on birefringent samples where the polarized light interacts strongly with the sample and so generates contrast with the background. Birefringence refers to the optical property of a material having a refractive index that depends on the polarization and propagation and direction of light. Such materials are optically anisotropic and are said to be birefringent (or birefractive). The birefringence is often quantified as the maximum difference between refractive indices exhibited by the material. Crystals with asymmetric crystal structures and plastics under mechanical stress are often birefringent.

Optical isotropy means having the same optical properties in all directions. An optically isotropic material may have crystallites that are smaller than a resolution limit, or have crystallites that are randomly oriented relative to each other and therefore have no measurable difference in orientation.

Polarized light microscopy is capable of distinguishing between isotropic and anisotropic substances. There are two polarizing filters in a polarizing microscope termed the polarizer and analyzer. A Michel-Levy Chart arises when polarized white light is passed through a birefringent sample. The Michel-Levy chart includes interference colors that describe optical retardance due to crystallite orientation. Retardance refers to the difference in phase shift between two characteristic polarizations of light upon reflection from an interface. Silver at the far left of the chart indicates very little orientation and the sequence of colors from right to left reveals increasing orientation.

Specifically, the PLM studies of the tubes showed that from the ID to about 50 microns from the ID, there is high induced polymer orientation. The polarized light micrographs of thin sections progressing from OD to ID show that that the outermost 40 to 50 microns of the expanded tube has a low anisotropy, as shown by a first order silver Michel-Levy color, an optical path difference (OPD) ca. 280 nm. However, a more strongly oriented region is observed in the innermost 50 to 70 microns exhibiting a first order gold to first order red, OPD of 420 to 560 nm. Thus, at about 50 to 70 microns from the ID, a transition was observed in the direction form inner to outer from high induced orientation to low orientation. The radial section from about 50 to 70 microns from the ID to the OD had little or no orientation. A semi-quantitative comparison of the magnitude of the gradient in orientation or anisotropy may be given as the change in retardance divided by the distance over which the change occurs, from the inner diameter to the outer diameter, which is 100% change over 50 microns.

It is believed that the gradient in orientation may be due in part to the significant difference in radial strain experienced between ID and OD of the extruded tubing during expansion. The degree of strain of the wall material decreases from the ID to the OD. Additionally, it is believed that the longer heat exposure of the outer surface and section to the heated glass mold results in faster relaxation of polymer chains in the radial section that causes a loss of induced orientation.

It is expected that with a high molecular weight polymer disclosed herein as compared the polymer in the above cited study, the relaxation time of the polymer chains is much longer and hence the orientation of the outer section will be better preserved.

Furthermore, higher expansion ratios for both hoop (>400%) and axial (>200%) directions may be achieved without resulting in the scaffolds being too brittle. The inventors have also found that when PLLA scaffolds also fabricated from resin with IV of 3.8 dL/g was expanded with expansion ratio of 500% at the hoop direction, cracks and fractures were seen. Higher molecular weight polymer creates additional toughness and strength through the effective transfer of load and dispersion of stress across multiple chains. This provides the capability to process the material into expanded tubing and lased scaffolds with higher orientation at both hoop and axial directions, rendering higher strength.

The expanded tube including the disclosed materials or the inventive scaffolds may have a high radial uniformity of polymer and crystal orientation through their thickness. The tubes or scaffolds may have a change in retardance as measured by PLM from the inner diameter to a selected distance to the outer diameter of less than 100%, less than 80%, less than 50%, less than 30%, less than 10%, 10 to 30%, 30 to 60%, or 60 to 80%. The selected distance may be 50%, 60%, 70%, 80%, 90%, 100%, 50 to 70%, 60 to 80%, 80 to 90%, or 90 to 100% of the thickness of the scaffold. The polymer composition, molecular weight of the tube, the radial expansion conditions, or any combination may be adjusted to obtain any of these ranges in changes in retardance.

The degree of crystallinity of the pre-cut tube or scaffold prior to the processing may be less than 5%, 1 to 5%, 5 to 10%, less than 10%, 10 to 15%, less than 30%, or 15 to 30%. In an embodiment, the crystallinity prior to processing can be between 10-25%. The degree crystallinity of the processed tube, cut scaffold, crimped scaffold, sterilized scaffold, may be 20 to 30%, 20 to 25%, 30 to 40%, 40 to 45%, 45 to 50%, and greater than 50%.

The polymer of a scaffold may have a Young's modulus greater than 500 MPa, or more narrowly, 500 to 600 MPa, 600 to 700 MPa, or 700 to 1000 MPa. The polymer of a scaffold may have a flexural modulus of greater than 2.5 GPa, or more narrowly, 2.5 to 3 GPa, 3 to 5 GPa, 5 to 6 GPa, 6 to 10 GPa, 6 to 8 GPa, 8 to 10 GPa, or greater than 10 GPa. The properties of the scaffold can be adjusted with enhanced processing that are disclosed herein. The properties disclosed for the scaffolds disclosed herein may refer to the properties of the scaffold in a finished state, before or after sterilization.

The various embodiments of the device may be configured to eventually completely absorb from an implant site. The device may provide drug delivery once implanted, provide mechanical support to the vessel, and then gradually completely absorb away. The device may also be configured to provide no mechanical support to a vessel and serve primarily as a drug delivery vehicle. The device may be configured to completely erode away within 6 months, 6 to 12 months, 12 to 18 months, 18 months to 2 years, or greater than 2 years.

A completely bioresorbable device may still include some nonbiodegradable elements such as radiopaque markers or particulate additives. The polymers of the device can be biostable, bioresorbable, bioabsorbable, biodegradable, or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, by hydrolysis and metabolic processes.

A scaffold may have a tendency to decrease in diameter or recoil (e.g., 2 to 10%) right after implantation (i.e., less than about 30 minutes post-implantation) as well as over a period of days, weeks, or months. Once implanted, the device may not have radial strength sufficient to reduce or prevent the immediate or long-term recoil.

The mechanical properties of the scaffold material disclosed herein may include elongation at break (ultimate elongation), tensile modulus, and strength. The scaffold polymer or material may have an elongation at break less than 5%, 5 to 10%, 10 to 25%, 25 to 50%, 50 to 100%, 100 to 200%, 200 to 400%, or greater than 400% at 25 deg C., 37° C., or in a range of 25 to 37° C. in a dry state or in a wet state. The scaffold polymer or material may have a tensile modulus less than 100 MPa, 100 to 2600 Mpa, 100 to 200 MPa, 200 to 400 MPa, 400 to 600 MPa, 600 to 800 MPa, 800 to 1000 MPa, 1000 to 1200 MPa, 1200 to 1400 MPa, 1400 to 1600 MPa, 1600 to 1800 MPa, 1800 to 2000 MPa, 2000 to 2200 MPa, 2200 to 2400 MPa, 2400 to 2600 MPa, or greater than 2600 MPa at 25 deg C., 37° C., or in a range of 25 to 37° C. in a dry state or in a wet state. The wet state may correspond to soaking the material for at least 2 minutes in a simulated body fluid such as a phosphate buffered saline solution.

Drug delivery from the device can be provided from a coating on a surface of the stent body of the device. The coating may be in the form a neat drug. Alternatively, the coating may include a polymer matrix with the drug mixed or dissolved in the polymer. The polymer matrix can be bioresorbable. Suitable polymers for the drug delivery polymer can include any PLA-based polymer disclosed herein, any other polymers disclosed herein, and copolymers and blends thereof in any combination.

The coating can be formed by mixing the polymer and the drug in a solvent and applying the solution to the surface of the device. The drug release rate may be controlled by adjusting the ratio of drug and polymeric coating material. The drug may be released from the coating over a period of one to two weeks, up to one month, one to three months, one to four months, up to three months, or up to four months after implantation. Thickness of the coating on the device body may 1 to 20 microns, 1 to 2 microns, 1 to 5 microns, 2 to 5 microns, 3 to 5 microns, 5 to 10 microns, or 10 to 20 microns. In some embodiments, the stent body of the device includes a drug release coating and the body is free of drug, aside from any incidental migration of drug into the body from the coating. The Mn of the coating polymer may be less than 40 kDa, 40 to 60 kDa, 60 to 80 kDa, 80 to 100 kDa.

Alternatively or additionally, the drug can also be embedded or dispersed into the body of device, and be slowly released up to months (e.g., one to three months or three to six months after implantation) and while the device is degrading. In this case, the drug can be included with the polymer when the tube is formed that is used to form the device. For example, the drug can be included in the polymer melt during extrusion or injection molding or in a solution when the tube is formed from dipping or spraying or casting.

The final device can be balloon expandable or self expandable. In the case of a balloon expandable device, the geometry of the device can be an open-cell structure similar to the stent patterns disclosed herein or closed cell structure, each formed through laser cutting a hollow thin-walled tube.

In a balloon expandable device, when the device is crimped from a fabricated diameter to a crimped or delivery diameter onto a balloon, structural elements plastically deform. The device may have minimal recoil outward so the delivery diameter may different slightly from the crimped diameter. Aside from this minimal recoil, the device retains a crimped or delivery diameter without an inward force on the balloon due to the plastically deformed structural elements.

The device is radially expandable at, for example, 37° C. in body fluid or simulated body fluid. When the device is expanded by a balloon, the structural elements plastically deform. The device is expanded to an intended expansion or deployment diameter and retains the intended expansion diameter or a diameter slightly less due to acute recoil inward due to inward pressure from the vessel during the about the first 30 minutes. The diameter may vary slightly after the acute period due to biological interactions with the vessel, stress relaxation, or both. At the final expanded diameter, the device does not exert any chronic outward force, which is a radial outward force exerted by the device in excess of the radial inward force exerted by the vessel on device.

In the case of a self-expandable device, when the device is compressed from a fabricated diameter to a delivery diameter on a balloon, the structural elements deform elastically. Therefore, to retain the device at the delivery diameter, the device is restrained in some manner with an inward force, for example with a sheath or a band. The compressed device is expanded to an intended expansion or deployment diameter by removing the inward restraining force which allows the device to self-expand to the intended deployment diameter. The structural elements deform elastically as the device self-expands. If the final expansion diameter is the same as the fabricated diameter, the device does not exert any chronic outward force. If the final expansion diameter is less than the fabricated diameter, the device does exert a chronic outward force.

The geometric structure of the device is not limited to any particular stent pattern or geometry. The device can have the form of a tubular scaffold structure that is composed of a plurality of ring struts and link struts. The ring struts form a plurality of cylindrical rings arranged about the cylindrical axis. The rings are connected by the link struts. The scaffold comprises an open framework of struts and links that define a generally tubular body with gaps in the body defined by the rings and struts.

This open framework of struts and links may be formed from a thin-walled cylindrical tube by a laser cutting device that cuts such a pattern into the thin-walled tube that may initially have no gaps in the tube wall. The scaffold may also be fabricated from a sheet by rolling and bonding the sheet to form the tube.

A stent or scaffold may have lengths of between 8 and 18 mm, 18 and 36 mm, 36 and 40 mm or even between 40 and 200 mm as fabricated or when implanted in an artery. Exemplary lengths include 12 mm, 14 mm, 18 mm, 24 mm, or 48 mm. The scaffold may have a pre-crimping or as-fabricated diameter of 2 to 3 mm, 2.5 to 3.5 mm, 3 to 4 mm, 3 to 5 mm, 5 to 10 mm, 6 to 8 mm, or any value between and including these endpoints. Diameter may refer to the inner diameter or outer diameter of the scaffold. Exemplary diameters include 2.5 mm, 3.0 mm, 3.25 mm, 3.5 mm, 4 mm, 5 mm, or 6 mm. The struts of the scaffold may have a radial wall thickness or width of 150 microns, 80 to 100 microns, 100 to 150 microns, 150 to 200 microns, 200 to 250 microns, 250 to 300 microns, 300 to 350 microns, 350 to 400 microns, or greater than 400 microns. Any combination of these ranges for radial wall thickness and width may be used.

The scaffold may be configured for being deployed by a non-compliant or semi-compliant balloon from a delivery diameter of 0.8 to 1 mm, 1 to 1.2 mm, 1.2 to 1.4 mm, 1.4 to 1.6 mm, 1.6 to 1.8 mm, and 1.8 to 2.2 mm, 1 mm, 1.2 mm, 1.3 mm, 1.4, mm, 1.6 mm, 1.8 mm, or 2 mm. Exemplary balloon sizes include 2.5 mm, 3 mm, 3.5 mm, 4 mm, 5.5 mm, 5 mm, 5.5 mm, 6 mm, 6.5 mm, 7 mm, or 8 mm, where the balloon size refers to a nominal inflated or deployment diameter of the balloon. The scaffold may be deployed to a diameter of between 2.5 mm and 3 mm, 3 mm and 3.5 mm, 3.5 mm and 4 mm, 4 mm and 10 mm, 7 and 9 mm, or any value between and including the endpoints. Embodiments of the invention include the scaffold in a crimped or delivery diameter over and in contact with a deflated catheter balloon.

The intended deployment diameter may correspond to, but is not limited to, the nominal deployment diameter of a catheter balloon which is configured to expand the scaffold. A device scaffold may be laser cut from a tube (i.e., a pre-cut tube) that is less than an intended deployment diameter. In this case, the pre-cut tube diameter may be 0.5 to 1 times the intended deployment diameter or any value in between and including the endpoints.

A device scaffold may be laser cut from a tube (i.e., a pre-cut tube) that is greater than an intended deployment diameter. In this case, the pre-cut tube diameter may be 1 to 1.5 times the intended deployment diameter, or any value in between and including the endpoints.

The device of the present invention may have a selected high crush recovery and crush resistance. Crush recovery describes the recovery of a tubular device subjected to a pinch or crush load. Scaffolds having a high crush recovery are particularly useful for treatment of the superficial femoral artery since upon implantation a scaffold is subjected to high crushing forces. The crush recovery can be described as the percent recovery to the device pre-crush shape or diameter from a certain percent crushed shape or diameter. Crush resistance is the minimum force required to cause a permanent deformation of a scaffold. The crush recovery and crush resistance can be based on a pre-crush shape or diameter of an as-fabricated device prior to crimping and expansion or a device after it has been crimped and expanded to an intended deployment diameter. The crush recovery of the device can be such that the device attains greater than about 70%, 80% or 90% of its diameter after being crushed to at least 50% of its pre-crush diameter.

The crush recovery and crush resistance of a balloon expandable scaffold that undergoes plastic deformation when crimped and deployed depend both on the scaffold material and scaffold pattern. Exemplary crush recoverable balloon expandable scaffold patterns can be found in US 2011/0190872 and US 2014/0067044.

A coating may be formed over the scaffold by mixing a coating polymer (e.g., a PLA polymer) and a drug (e.g., a macrocyclic drug) in a solvent and applying the solution to the surface of the scaffold. The application may be performed by spraying, dipping, ink-jet printing, or rolling the scaffold in the solution. The coating may be formed as a series of layers by spraying or dipping followed by a step to remove all or most of residual solvent via, for example, evaporation by heating. The steps may then be repeated until a desired coating thickness is achieved.

The drug release rate may be controlled by adjusting the ratio of drug and polymeric coating material. The drug to polymer ratio may be between 5:1 to 1:5. The drug may be released from the coating over a period of one to two weeks, up to one month, or up to three months after implantation. Thickness or average thickness of the coating on the device body may be less than 4 microns, 3 microns, 2.5 microns, 1 to 20 microns, 1 to 2 microns, 2 to 3 microns, 2 to 2.9 microns, 2 to 2.5 microns, 1 to 5 microns, 2 to 5 microns, 3 to 5 microns, 5 to 10 microns, or 10 to 20 microns. The coating may be over part of the surface or the entire surface of a scaffold substrate. In some embodiments, the body of the device includes a drug release coating and the body is free of drug, aside from any incidental migration of drug into the body from the coating.

In some embodiments, the coating may include a primer layer between the scaffold body or structure and a drug delivery coating layer to enhance the adhesion of the drug coating to the scaffold. Alternatively, the coating may have no primer layer and only a drug delivery coating layer.

The coated scaffold may then be crimping over a delivery balloon. The crimped scaffold may then be packaged and then sterilized with radiation such as electron-beam (E-Beam) radiation or a low temperature ethylene oxide process (see e.g., US 2013/0032967). The range of E-beam exposure may be between 20 and 30 kGy, 25 to 35 kGy, or 25 to 30 kGy.

The device body may include or may be coated with one or more therapeutic agents, including an antiproliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, novolimus, myolimus, deforolimus, umirolimus, biolimus, merilimus, temsirolimus structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxyl)propyl-rapamycin, 40-O-[2-(2-hydroxyl)ethoxy] ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, novolimus, myolimus, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, anti-thrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

"Molecular weight" refers to either number average molecular weight (Mn) or weight average molecular weight (Mw). References to molecular weight (MW) herein refer to either Mn or Mw, unless otherwise specified. The Mn may be as measured by Gel Permeation Chromatography with refractive index detection relative to polystyrene standards. Suitable mobile phase solvents are acetone, tetrahydrofuran, chloroform, 1,1,1-trichloroethane, 2,2,2-trifluoroethanol, and hexafluoro-2-propanol, "Semi-crystalline polymer" and other terms relating to crystalline polymer may be as defined in Pure Appl. Chem., Vol. 83, No. 10, pp. 1831-1871, 2011. Semi-crystalline polymer refers to a polymer that has or can have regions of crystalline molecular structure and amorphous regions. The crystalline regions may be referred to as crystallites, lamella, or spherulites which can be dispersed or embedded within amorphous regions.

The "degree of crystallinity" may be expressed in terms of, $w_c$ (mass fraction), $\phi_c$ (volume fraction) and refers to mass fraction or volume fraction of crystalline phase in a sample of polymer. The mass-fraction and the volume-fraction degrees of crystallinity are related by the equation, $w_c = \phi_c \rho / \rho_c$, where $\rho$ and $\rho_c$ are the mass concentrations (mass densities) of the entire sample and of the crystalline phase, respectively. The degree of crystallinity can be determined by several experimental techniques. Among the most commonly used are: (i) x-ray diffraction, (ii) calorimetry, (iii) mass density measurements, (iv) infrared spectroscopy (IR), (v) solid-state NMR spectroscopy, and (vi) vapor permeability.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

"Elastic deformation" refers to deformation of a body in which the applied stress is small enough so that the object retains, substantially retains, or moves towards its original dimensions once the stress is released.

The term "plastic deformation" refers to permanent deformation that occurs in a material under stress after elastic limits have been exceeded.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" and "stiffness" may be defined as the ratio of a component of stress or force per unit area applied to a material divided by the strain along an axis of applied force that results from the applied force. The modulus or the stiffness typically is the initial slope of a stress-strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Elongation at break" or "ultimate elongation" is the elongation recorded at the moment of rupture of a specimen in a tensile elongation test, expressed as a percentage of the original length or the strain.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising:
   a bioresorbable polymer scaffold comprising a polymer combination including a polylactide polymer and polycaprolactone,
   wherein the polymer combination is a blend of poly(L-lactide) (PLLA) and 70/30 poly(L-lactide-co-caprolactone) random copolymer, wherein caprolactone units of the copolymer are 1 to 5 wt % of the blend,
   wherein the scaffold includes a plurality of interconnected struts,
   wherein a thickness of the struts is 80 to 100 microns and a width of the struts is 200 to 250 microns, and
   wherein the scaffold has a crimped state and a deployed state and a radial strength of the scaffold when expanded from the crimped state to the deployed state in saline or bodily fluid at 37° C. is at least 650 mm Hg.

2. The stent of claim 1, wherein a hoop ultimate tensile strength is at least 25% greater than an axial ultimate tensile strength of the scaffold.

3. The stent of claim 1, wherein a concentration of unreacted lactide monomer in the scaffold is 0.5 to 1 wt %.

4. The stent of claim 1, wherein a number average molecular weight (Mn) of the polymer combination is less than 60 kDa at 1 year of exposure of the scaffold to saline or bodily fluids at 37° C.

5. The stent of claim 1, wherein a crystallinity of the scaffold is 25% to 50%.

6. The stent of claim 1, wherein a change in retardance as measured by polarized light microscopy (PLM) from an inner diameter to 50% of the thickness to the outer diameter of the scaffold is less than 50%.

7. A stent comprising:
   a bioresorbable polymer scaffold comprising a polymer formulation including a blend of polylactide (PLA) polymer and a PLA and polycaprolactone (PCL) copolymer,
   wherein the PLA polymer is poly(L-lactide) (PLLA) and the copolymer is 70/30 poly(L-lactide-co-caprolactone) random copolymer, wherein caprolactone units of the copolymer are 1 to 5 wt % of the blend,
   wherein the scaffold includes a plurality of interconnected struts,
   wherein a thickness of the struts is 80 to 100 microns and a width of the struts is 200 to 250 microns,
   wherein a number average molecular weight (Mn) of the blend is greater than 60 kDa, and
   wherein the scaffold has a crimped state and a deployed state and a radial strength of the scaffold when expanded from the crimped state to the deployed state in saline or bodily fluid at 37° C. is at least 650 mm Hg.

8. The stent of claim 1, wherein a number average molecular weight (Mn) of a polymer of the polymer combination is greater than 110 kDa.

* * * * *